(12) United States Patent
Gnann (10) Patent No.: US 12,419,273 B2
(45) Date of Patent: Sep. 23, 2025

(54) METHOD FOR PRODUCTION OF MILK WITH A HIGH CONTENT OF NATIVE VITAMIN D

(71) Applicant: Tony Gnann, Munich (DE)

(72) Inventor: Tony Gnann, Munich (DE)

( * ) Notice: Subject to any disclaimer, the term of this patent is extended or adjusted under 35 U.S.C. 154(b) by 897 days.

(21) Appl. No.: 15/548,495

(22) PCT Filed: Feb. 1, 2016

(86) PCT No.: PCT/EP2016/052031
§ 371 (c)(1),
(2) Date: Aug. 3, 2017

(87) PCT Pub. No.: WO2016/124521
PCT Pub. Date: Aug. 11, 2016

(65) Prior Publication Data
US 2018/0000043 A1    Jan. 4, 2018

(30) Foreign Application Priority Data
Feb. 4, 2015 (EP) .................................. 15153835

(51) Int. Cl.
*A01J 5/007* (2006.01)
*A01K 1/12* (2006.01)
(Continued)

(52) U.S. Cl.
CPC ................ *A01K 1/12* (2013.01); *A01K 29/00* (2013.01); *A23C 9/158* (2013.01); *A61N 5/00* (2013.01);
(Continued)

(58) Field of Classification Search
CPC .. A01K 1/12; A01K 29/00; A01J 5/007; A01J 5/0131; A01J 5/0135
See application file for complete search history.

(56) References Cited

U.S. PATENT DOCUMENTS 4,755,711 A * 7/1988 Fields ..................... F21V 7/22
    313/111
8,003,130 B2   8/2011 Gnann
(Continued)

FOREIGN PATENT DOCUMENTS

CN       104168953 A     10/2016
DE    102005059518 A1     6/2007
(Continued)

OTHER PUBLICATIONS

PCT Translation of International Preliminary Report on Patentability and International Search Report from PCT/EP2016/052031.
(Continued)

*Primary Examiner* — Son T Nguyen
(74) *Attorney, Agent, or Firm* — Lippes Mathias LLP (57) ABSTRACT

The invention relates to a method for the production of milk with a high content of native vitamin D3, comprising the irradiation of one or more lactating animals in a roofed
(Continued)

enclosure, having at least one luminaire with a lamp emitting UV-A and UV-B radiation, and the milking of animals. The method allows producing milk having a high content of native vitamin D. The method also leads to an improved milk yield per animal.

17 Claims, 2 Drawing Sheets

(51) Int. Cl.
    *A01K 29/00*     (2006.01)
    *A23C 9/158*     (2006.01)
    *A61N 5/00*     (2006.01)
    *A61N 5/06*     (2006.01)

(52) U.S. Cl.
    CPC ........ *A61N 5/0613* (2013.01); *A23C 2230/15* (2013.01); *A23V 2002/00* (2013.01); *A61N 2005/064* (2013.01); *A61N 2005/0651* (2013.01); *A61N 2005/0654* (2013.01); *A61N 2005/0661* (2013.01)

(56) References Cited

U.S. PATENT DOCUMENTS

| | | | |
|---|---|---|---|
| 2002/0047516 A1* | 4/2002 | Iwasa | G09F 13/20 313/512 |
| 2010/0287830 A1* | 11/2010 | Chen | A01G 7/045 47/58.1 LS |
| 2012/0262917 A1* | 10/2012 | Courcelle | F21V 15/01 362/235 |
| 2013/0172963 A1 | 7/2013 | Moffat | |

FOREIGN PATENT DOCUMENTS

| | | | |
|---|---|---|---|
| EP | 1970423 A1 | 9/2008 | |
| EP | 1841325 B1 * | 7/2010 | ............ A01K 29/00 |
| EP | 2573799 A1 | 3/2013 | |
| RU | 2084045 C1 | 8/1996 | |
| RU | 38892 U1 | 7/2004 | |
| RU | 2409191 C2 | 11/2006 | |
| RU | 2378736 C1 | 1/2010 | |
| WO | 84/000693 A1 | 3/1984 | |
| WO | WO-2010016009 A1 * | 2/2010 | ........... A61N 5/0613 |
| WO | 2014184277 A1 | 11/2014 | |

OTHER PUBLICATIONS

PCT International Search Report, PCT/EP2016/052031.

* cited by examiner

METHOD FOR PRODUCTION OF MILK WITH A HIGH CONTENT OF NATIVE VITAMIN D

The method relates to a method for the production of milk with a high content of native vitamin D3.

Vitamin D plays a pivotal role in humans and animals in the regulation of the calcium and phosphate metabolism. Vitamin D deficiency results in considerable defects in bone formation and may lead to rickets in children and to softening of the bones in grownups. Sufficient vitamin D generates a potent immunization and may act preventatively against some chronic diseases.

Vitamin D deficiency may occur in humans in the northern hemisphere especially in autumn and winter. Foodstuffs only have low vitamin D contents, except in cod liver oil and fatty fish. The artificial fortification of vitamin D in foodstuffs by adding synthetically produced vitamin D is not permitted, at least not in Germany. Synthetic vitamin D may be produced synthetically or obtained from natural sources such as fish liver oils.

European regulation (EU) 1169/2011 recommends a daily vitamin D dose of 5 µg. The vitamin D3 content in commercially available cows' milk is according to current Bundeslebensmittelschlüssel [Federal Food Index] (version 3.01) 0.1 µg/100 g, which only accounts for 2% of the recommended daily dose. This means that the milk which is currently available is not suitable for making a significant contribution to the vitamin D requirement.

Loose housing for lactating mammals, especially dairy cows, which is currently usual for substantial herds of animals means that the animals are free to roam within the animal house and are free to seek out the places where they lie down, eat and are milked, both during the day and in the night. During the days, the cow sheds are usually illuminated by luminaires and during the night, they are equipped with emergency lighting, which is quiet in most cases.

The problem of the present invention was to provide a method for the production of milk with an increased vitamin D content. Here, it was intended to increase the natural vitamin D content of the milk. It was intended that the method should also be suitable especially for an increased number of animals.

Surprisingly, these problems could be addressed by a method for the production of milk in which one or more lactating animals are irradiated in a roofed enclosure, preferably an animal house, with at least one luminaire comprising a lamp which emits UV-A radiation and UV-B radiation, as the animals are milked.

Using the method according to the invention, it was possible, surprisingly, to produce milk with a very high vitamin D3 content of more than 0.5 µg/100 ml, even in the range of from 1.5 to above 4 µg/100 ml. With this milk it is possible to meet most of a human's daily vitamin D requirement, indeed all of the human's vitamin D requirement. Moreover, the milk produced according to the invention is a normal foodstuff since the vitamin D3 which it contains is native vitamin D3.

Native vitamin D3 in the milk is produced naturally in the lactating animal. Vitamin D3 that is added to the milk after milking is not native vitamin D3. Vitamin D is herein below understood to mean vitamin D3.

Lactating animals are female mammals which give milk, sheep, cows and goats being especially suitable. The lactating animals are preferably cows. One or more lactating animals are kept in the roofed enclosure, especially an animal house, preferably at least 10, more preferably at least 50 or 100, or even more than 200 animals.

The roofed enclosure is preferably an animal house. The roofed enclosure may also be a simple housing or a shelter. The roofed enclosure is preferably an animal house in the form of a closed building.

A luminaire is a device which includes a lamp as light source and which is suitable for illumination purposes. For the purposes of the present invention, the irradiation with UV light is also understood to mean an illumination. A lamp is also referred to as an illuminant. According to the invention, one or more luminaires may be used for illuminating the covered enclosure and/or for irradiating the animals. The luminaire used according to the invention comprises a lamp which emits UV-A radiation and UV-B radiation, i.e. the lamp has an emission spectrum which includes components in the UV-A range and in the UV-B range.

In the present context, the emission spectrum of the lamp is understood as meaning the radiation emitted in the wavelength range of from 200 nm to 780 nm. According to DIN 5031-7, the following subdivision applies:

| visible light (VIS) | from 380 to 780 nm |
|---|---|
| UV-A radiation | from 315 to 380 nm |
| UV-B radiation | from 280 to 315 nm |
| UV-C radiation | from 200 to 280 nm |

The lamps used according to the invention have components in the UV-A range and components in the UV-B range in the emission spectrum. While lamps which are usually employed for illumination purposes have an emission spectrum which sometimes includes components in the UV-A range, components in the UV-B range are usually not present.

The radiation component in the UV-B range in the emission spectrum of the lamp is for example at least 0.1%, preferably at least 0.2% and especially preferably at least 0.5%. As a rule, it is preferred that the radiation component in the UV-B range in the emission spectrum of the lamp is less than 5%, preferably less than 4%, especially preferably less than 2%. The component relates to the percentage irradiation intensity of the lamp in the UV-B range in relation to the overall irradiation intensity of the lamp in the emission spectrum in the wavelength range of from 200 to 780 nm.

The radiation component in the UV-A range in the emission spectrum of the lamp can be for example at least 0.5%, is preferably at least 1% and especially preferably at least 4.5%. As a rule, it is preferred that the radiation component in the UV-A range in the emission spectrum of the lamp is less than 20%, preferably less than 15%. The component relates to the percentage irradiation intensity of the lamp in the UV-A range in relation to the overall irradiation intensity of the lamp in the emission spectrum in the wavelength range of from 200 to 780 nm.

The lamp preferably also includes visible light in the emission spectrum, for example an radiation component in the VIS range in the emission spectrum of the lamp of at least 50%, preferably at least 70% and especially preferably at least 80%. The component refers to the percentage of the irradiation intensity of the lamp in the VIS range in relation to the overall irradiation intensity of the lamp in the emission spectrum in the wavelength range of from 200 to 780 nm. The lamp preferably emits white light.

Lamp-specific parameters such as irradiation intensity (unit $W/m^2$) are defined in DIN 5031. The spectral irradiation intensity indicates how much irradiation intensity exists in a certain wavelength range. The spectral irradiation intensities or their percentages can be determined for example using a spectrometer or spectroradiometer. As a rule, information regarding the percentages of the spectral irradiation intensities can be found in the lamps' data sheets.

The Color Rendering Index (CRI) is a characteristic on a scale of from 0 to 100 which describes the quality of the color rendering of light sources. The lamp used according to the invention preferably has a Color Rendering Index of greater than 40, especially greater than 70 and especially preferably greater than 80. The color rendering index can be determined according to the Commission Internationale de l'Eclairage, Method of Measuring and Specifying Color Rendering Properties of Light Sources, Publ. CIE 13.3-1995, 1995.

Any lamp which emits UV-A radiation and UV-B radiation may be used as the lamp. For example, the lamp may be a full-spectrum lamp or a UV lamp, a full-spectrum lamp being preferred. As a rule, full-spectrum lamps have a color rendering index of greater than 70 and preferably greater than 80. The color temperature of full-spectrum lamps is, as a rule, at least 5000 K.

While UV lamps may be employed, they are less preferred. Due to the high UV component in UV lamps, care must be taken that the animals do not receive an unduly high irradiation dose. This may be achieved for example by a shorter irradiation time. When using UV lamps, the use of additional, normal lamps for illumination with visible light is furthermore necessary as a rule. This is not necessary for example when employing full-spectrum lamps, which are capable of emitting UV-A radiation and UV-B radiation, since these lamps simultaneously provide the illumination with visible light.

The lamp may be for example a gas discharge lamp, a fluorescent lamp, a halogen metal vapor lamp or an LED lamp. LEDs (light-emitting diodes) are also referred to as electroluminescent diodes. LED lamps which emit components in the UV-A range and in the UV-B range are well-suited. The LED lamps which emit components in the UV-A range and in the UV-B range are preferably white LED lamps, i.e. lamps which also emit white light. An advantage with LED lamps is also their low energy consumption. The gas discharge lamps may be low-pressure discharge lamps or high-pressure discharge lamps. Fluorescent lamps are, as a rule, low-pressure discharge lamps. Halogen metal vapor lamps are, as a rule, high-pressure discharge lamps.

The lamp is especially preferably a fluorescent lamp. In fluorescent lamps, fluorescent substances generate, via physico-chemical processes, visible radiation/light (380 to 780 nm) or UV radiation in a wavelength range of from approx. 280-380 nm and as the case may be also below 280 nm. As a rule, fluorescent substances are inorganic compounds, usually salts or in some cases also oxides which are ultrapure but additionally include so-called doping impurities or activators. The chemical structure in combination with unoccupied sites determines the fluorescent substances' emission properties.

According to the usual nomenclature for a fluorescent substance, it is the compound employed and the activator, or the doping agent, which are indicated, and these are separated by a colon. Strontium borophosphate:Eu, for example, is europium-doped strontium borophosphate.

Usual fluorescent lamps are so-called three-band lamps, which generate white light by mixing red-, green- and blue-emitting radiation. It is known that green-emitting fluorescent substances also emit in the UV-A range, and an Hg emission exists at 365 nm. Therefore, such three-band lamps also emit in the UV-A range (approx. 2 to 4%), but not in the UV-B range. The component in the VIS range is, as a rule, approximately from 96 to 98%.

If UV-emitting fluorescent substances are used in fluorescent lamps for certain applications, they give rise to an emission which is caused by the fluorescent substances, but which, owing to the wave-length-dependent glass transmission of the lamp bulb, is absorbed more in the shorter-wave UV range. If it is intended to generate fluorescent lamps with an emission spectrum in the VIS, in the UV-A and the UV-B range, a mixture of fluorescent substances which emit in the light range, in the UV-A and in the UV-B range is necessary. Fluorescent substances for UV-B are known. The fluorescent lamp may, for example, comprise fluorescent substances selected from among $SrAl_{12}O_{19}$:Ce, $LaB_3O_6$:Bi,Gd or $LaPO_4$:Ce.

An example of a suitable fluorescent lamp is, for example, a fluorescent lamp which comprises, as fluorescent substances, strontium borophosphate:Eu (SBPE), strontium magnesium phosphate:Sn (SMS), barium magnesium aluminate:Ce (BAC) and, if desired, lanthanum phosphate:Ce (LAP). A fluorescent lamp with a mixture of approx. 36% SBPE, approx. 50% SMS, approx. 13% BAC and a maximum of 1% LAP in combination with a known glass transmission, for example, generates an irradiation intensity which is composed as follows: VIS component (380-780 nm): max. 90%, UV-A component (315-380 nm): max. 10%, UV-B component (280-315 nm): max. 1% and UV-C component (200-280 nm): 0%.

The use of the luminaire with a lamp which emits UV-A radiation and UV-B radiation results in a stimulation, controlled via the light regimen, of the vitamin D3 secretion via the animals' skin. This results in an increased vitamin D3 concentration in the blood plasma. The vitamin D3 content in the blood plasma, in turn, correlates with the vitamin D3 concentration in the milk.

In enclosures for agricultural livestock, especially in animal houses, a considerable risk of fire must be expected as the result of the storage and handling of readily flammable substances such as feedstuffs, hay, straw and the like, caused by dust or fibers. Therefore, due to legal requirements, luminaires which may be used as a rule are only those which have a high degree of protection and, moreover, are marked with the sign. In addition, the air in animal houses is more or less high in moisture and ammonia, which rapidly leads to corrosion damage in unsuitable luminaires and therefore to their failure and destruction. At least in Germany, IP 65-rated luminaires are therefore mandatory in enclosures of agricultural livestock, especially in animal houses.

The IP ratings according to DIN 60529 specify to what extent a lamp is protected against foreign objects and water. A rating of IP 65 for example means that the luminaire is dustproof and protected against strong water jets.

The lamp may be protected for example by a housing and/or a lamp cover, sometimes also referred to as a lamp enclosure. Naturally, the lamp cover must be permeable to light emitted by the lamp. Luminaires with lamp enclosures or lamp covers made of glass or plastics material are conventional. While these lamp covers are permeable to visible light, as desired, they almost completely reduce the transmission of UV rays, if present, especially in the UV-B range.

Thus, normal glass (soda lime glass), especially window glass, is not permeable to UV radiation of below 320 nm. Borosilicate glass, in contrast, is permeable to UV radiation down to approximately 290 nm. Quartz glass is permeable down to approximately 200 nm. Plastids material are frequently sensitive to UV radiation. Depending on their embodiment, some plastics materials may also be designed to be UV permeable. Thus, there are embodiments of polymethyl methacrylate (PMMA) which are UV-permeable. Further UV-permeable plastics materials are polymethylpentene, fluorinated ethylene-propylene (FEP) or polytetrafluoroethylene (PTFE).

Plastics materials frequently contain UV stabilizers. The UV permeability of certain plastics materials may be adjusted for example by the type and the amount of the UV stabilizers employed. UV-permeable plastics materials, for example UV-permeable plexiglass, are commercially available.

In a preferred embodiment, the luminaire comprises a lamp cover which is permeable to UV-B radiation with a wavelength of 300 nm. The degree of transmission of the lamp cover at a wavelength of 300 nm is, for example, at least 20%, preferably at least 40%, especially preferably at least 50% and most preferably at least 60%.

In a preferred embodiment, the luminaire comprises a lamp cover which is permeable to UV-B radiation of the lamp, the lamp cover preferably having a permeability of at least 20%, preferably at least 40%, especially preferably at least 60%, for the UV-B radiation emitted by the lamp.

The lamp cover is preferably formed from quartz glass, borosilicate glass, polymethyl methacrylate (PMMA or plexiglass), polymethylpentene, fluorinated ethylene propylene (FEP) or polytetrafluoroethylene (PTFE). The material of the lamp cover may, naturally, contain additional agents or additives.

In a preferred embodiment, the luminaire comprises a housing and a lamp cover, a seal being arranged between the housing of the luminaire and the lamp cover. The seal may be made for example of silicon, polyurethane or rubber, for example EPDM (ethylene propylene diene), polyurethane being preferred. Owing to the seal, the penetration of foreign substances into the luminaire may be avoided or reduced markedly. The seal, for example a seal made of polyurethane, is preferably a seal to which talcum, usually in the form of a powder, has been applied. The talcum may, for example, simply be rubbed or brushed onto the seal in the form of a powder, or else a composition of talcum powder and water is used for the application.

It is known that sealants can be attacked by UV-B radiation. Thus, in experiments which have been carried out it has been shown that upon operation of the luminaires according to the invention which contained a seal, damage to the seal could be observed over time, which adversely affects the tightness of the luminaire and the detachability of the lamp enclosure, for example for maintenance work. Such damage to the seal did not occur when a seal was talcum applied thereto was employed.

One or more lactating animals are irradiated in a roofed enclosure which includes at least one luminaire comprising a lamp which emits UV-A radiation and UV-B radiation. To this end, the roofed enclosure is illuminated with the luminaire(s). The number and the distribution of the luminaires in the roofed enclosure depend for example on the nature and the size of the roofed enclosures, the desired illumination intensity and the nature of the luminaires. It is possible to use the light programs which are customary for illuminating animal houses.

The duration of the irradiation of the lactating animals in a roofed enclosure, especially an animal house, with at least one luminaire comprising a lamp which emits UV-A radiation and UV-B radiation may vary within wide ranges and depends for example on the UV component of the lamp and the irradiation intensity.

The half-life of vitamin D in the organism is relatively long. Half-lives of approximately 19 days are cited. The vitamin D content therefore only drops gradually when the irradiation according to the invention is stopped over a certain period of time. As a consequence, relatively long interruptions of days or even weeks between the irradiation intervals are quite possible, and it is still possible to obtain milk with an increased vitamin D3 content. Discontinuous irradiation is therefore possible, the UV dose applied being carried out over two or more days or weeks which are separate from each other.

Advantageously, the duration of the irradiation per week with the luminaire used according to the invention is, for example, at least 6 hours, preferably at least approximately 20 hours, more preferably at least approximately 50 hours. It may amount to, for example, less than 155 hours, preferably less than 135 hours, per week. The irradiation phases may be distributed relatively uniformly over the days of the week or else concentrated to one or more days, a relatively uniform distribution to the days of the week being preferred.

In a preferred embodiment, the lactating animals are irradiated per day for example for at least 1 hour, for example for 6 to 22 hours, expediently for approximately 8 to 20 hours per day with the luminaire used according to the invention. The daily irradiation can preferably be once; however, a discontinuous irradiation is also possible, the UV dose applied being carried out over two or more time intervals which are separate from each other. Even in the case of a photoperiod with daily irradiation it is possible to interrupt the irradiation on some days. Again, the vitamin D content is not substantially adversely affected in such a case.

The abovementioned ranges for the irradiation time are expedient especially when a full-spectrum lamp is used as the lamp. When employing a UV lamp, the UV-B component is markedly higher, as illustrated above, so that the duration of the radiation with a luminaire comprising a UV lamp should, as a rule, be markedly shorter, for example at least 0.5 hours per week, for example 3 hours to 15 hours per week or at least 0.1 hour per day, for example 0.5 to 2 hours per day. What has been said above as regards interruptions and continuous or discontinuous irradiation procedures applies correspondingly.

As already discussed, the luminaire preferably also emits visible light, preferably white light, so that the luminaire also serves to illuminate the roofed enclosure with visible light. The luminaire is therefore preferably also used for illuminating the roofed enclosure during the day phase. However, the use in the night phase and the use both in the night phase and in the day phase is also possible.

The illumination intensity which is obtained by the luminaire used according to the invention may amount for example to more than 80 lux, preferably more than 100 lux and more preferably more than 250 lux. The illumination intensity may amount to, for example, up to 500 lux or even more. The illumination intensity can be measured using customary lux meters. The illumination intensity specified refers to a measurement at a height of approximately 1.50 m above the ground of the roofed enclosure.

The photoperiod of the lactating animals can expediently be divided into a day phase with one light regimen and a night phase with another light regimen. The light programs which are customary for indoor-kept lactating animals can simply be kept, except that the luminaire used according to the invention is employed, for example to replace the luminaires usually employed for illumination with visible light.

In a preferred embodiment of the method according to the invention, the photoperiod of the animals is divided into a day phase with a first light regimen and a night phase with a second light regimen, the luminaire being employed for illumination purposes at least for some time during the day phase and/or a light source being employed during the night phase which emits light in the wavelength range of 500 nm or more and essentially no light in the wavelength range of below 500 nm.

In the day phase, the lactating animals in the roofed enclosure are provided with visible light of sufficient lightness by illumination. The night phase, being a resting phase, may include a darker light regimen, but as a rule it is expedient also to illuminate the roofed enclosure with visible light during the night phase so as to allow the animals to orientate themselves with ease.

The light regimen used is, in principle, controllable as desired in respect of intensity and timing. The respective phases may be shortened, elongated or shifted forwards or back as desired. However, it must be taken into consideration that animals are biological systems which react slowly and take a long time to change. After the beginning of the method according to the invention, a habituation phase of, for example, a few days, for example 30 days or more, may therefore be present until the vitamin D3 content in the milk becomes established in a new, elevated equilibrium. However, stopping the irradiation according to the invention for a few days only leads to a gradual return to the original state.

Irrespective of the fact that the use of light can be controlled as desired as regards time, it is advantageous for the day phase to last for example approximately 6 to 22 hours, preferably 8 to 20 hours, expediently approximately 12 to 21 hours and preferably approximately to 20 hours. A favorable duration is for example approximately 17 hours plus/minus 1 hour or more. The night phase may last for example approximately 2 to 16 hours, expediently approximately 3 to 12 hours and preferably approximately 4 to 10 hours. An especially advantageous duration lasts for example approximately 7 hours plus/minus 1 hour or less.

The luminaire according to the invention is preferably used for illuminating the roofed enclosure with visible light in the day phase. In this manner, the luminaire does not only deliver radiation in the UV-A and UV-B range, but also the illumination with visible light. Preferably, the lamp employed according to the invention is a full-spectrum lamp. The emission spectrum of full-spectrum lamps is closest to sunlight. In addition to the luminaire according to the invention, customary luminaires may be employed for illumination purposes in the day phase, if so desired.

In the night phase, the animals are preferably placed under a light regimen in which a light source is employed which emits light in the wavelength range of 500 nm or more and essentially no light in the wavelength range of below 500 nm. The light source used for the night phase emits especially light that is yellow, orange, amber or red in color, or a mixture. Therefore, the light source has an emission spectrum in the wavelength range of the visible light which shows the maximum value with a relative intensity of 100% at a wavelength of 500 nm or more.

The fact that the light source emits essentially no light with a wavelength of below 500 nm means in this context especially that any measurable value in the emission spectrum of the visible light below 500 nm, if present in the first place, has a relative intensity of less than 15%, preferably less than 10% and especially preferably less than 5 or less than 3%. Preferably, the light source employed emits essentially no light in the wavelength range of below 520 nm and more preferably below 540 nm. The light source employed especially preferably emits no light in the wavelength range of below 500 nm.

Light sources which can be used for the night phase may be, for example, customary lamps such as, for example, thermal emitters, continuum emitters, line emitters, gas discharge lamps, which contain a monochromator so that essentially no light with a wavelength of below 500 nm is emitted. Examples of monochromators are prisms, diffraction grooves and optical filters. In this manner it is possible to make for example red-light lamps.

However, it is preferred to employ light sources for the night phase which do not require a monochromator. It is preferred to use a luminescence emitter by way of light source. Luminescence emitters may be so-called line emitters or monochromatic emitters. Examples of luminescence emitters are gas discharge lamps and light-emitting diodes (LEDs).

The emission spectrum of the light source in the wavelength range of the visible light preferably has at least a maximum of over 550 nm, more preferably at least a maximum of over 570 nm and even more preferably over 600 nm.

An example of a suitable light source is a sodium vapor lamp (SVL). SVLs are gas discharge lamps which emit monochromatic yellow light with a wavelength of approximately 589 to 590 nm. An especially suitable light source for the night phase are LEDs. LED lamps allow the desired wavelength range to be adjusted in a targeted manner, and at the same time they have a sufficiently high photo-optic effect for the animals to be able to orientate themselves well when illuminated with these light sources.

Suitable LEDs are LED lamps with the light color red, amber (also called "super orange") (for example maximum approx. 612 nm), orange (for example maximum approx. 605 nm) or yellow (for example maximum approx. 585 nm) and mixed colors of the spectra. Preferred are red light-emitting diodes (for example maximum approx. 630 nm; including "ultra red" at a maximum of approx. 660 nm). Such LEDs are commercially available and can be obtained anywhere. Examples of commercially available LEDs are, for example, Lumileds® Luxeon red 1 watt, Lumileds® Luxeon Star/O red 1 watt or SOUL R32 red 1 watt.

The light source for the night phase, especially the LED lamp, is in operation during the night phase for, as a rule, at least 1 hour, preferably at least 2 hours, more preferably at least 5 hours and even more preferably at least 6 hours.

Surprisingly, the animals' environment can be illuminated with the abovementioned light sources in the night phase to provide relative lightness. The illumination intensity which is obtained by the light sources used in the night phase can preferably be more than 50 lux; however, illumination intensities of below 50 lux are also possible. In principle, it is possible to use high illumination intensities in the night phase, but as a rule, it is for example not more than 150 lux, more preferably not more than 100 lux. The illumination intensity in the night phase is for example at least 50 lux, preferably at least 100 lux, less than the illumination intensity in the day phase. As regards the measurement of the illumination intensity, reference is made to what has been said above.

The method furthermore comprises the milking of the animals. Milking can be carried out as usual. No changes are required. The animals may be milked for example once, twice, three times or more often per day. As usual, milking in the day phase, for example in the morning and in the evening or once in the day phase, is usually expedient. Alternatively or additionally, however, milking may also be done in the night phase.

It is clear that the irradiation of the animals with the at least one luminaire comprising a lamp which emits W-A radiation and UV-B radiation is, according to the invention, independent of the point in time of milking. Especially, milking may be done at points in time when this irradiation is carried out or this irradiation is not carried out.

Native vitamin D3 binds predominantly to fat molecules and proteins in the milk. Fat reduction therefore also means that the vitamin D3 content may be reduced. Native vitamin D3 is not sensitive to temperature.

Normal commercially available milk which is produced by the usual method has vitamin D contents of approx. 0.1 µg/100 ml milk (according to Bundeslebensmittel-schlüssel, state 2014). To produce commercially available milk, traditional lamps, for example incandescent bulbs, neon tubes or sodium vapor lamps, are employed during the day for illuminating the animal houses, in contrast to the inventive method. No irradiation with UV-B component is carried out.

The vitamin D3 content of the milk is determined by a standard HPLC/UV method. Alternatively, the vitamin D3 content may also be determined by ELISA (Enzyme Linked Immunosorbent Assay). With the aid of the ELISA, the vitamin D3 content in a sample such as milk can also be determined reliably and is used by way of standard in some countries. This was confirmed by test measurements in independent and certified analytical laboratories.

The milk produced by the method according to the invention has a markedly increased vitamin D3 content. For example, it may have a vitamin D3 content of more than 0.5 µg/100 ml milk, preferably more than 1 µg/100 ml milk and especially preferably more than 1.5 µg/100 ml milk, it being possible for example to obtain contents of from 1.5 to 4 µg/100 ml milk and more. The vitamin D3 of the milk is native vitamin D3. The specified values relate to the determination by means of ELISA or HPLC/UV, the vitamin D3 content being determined.

The method according to the invention increases the native vitamin D3 content of the milk. By an increased native vitamin D3 content there is meant especially a vitamin D3 content of at least 0.5 µg/100 ml milk, preferably more than 1 µg/100 ml milk and especially preferably more than 1.5 µg/100 ml milk.

Using the method according to the invention it is also possible to increase the milk yield per animal in comparison to a identical method in which, however, a normal lamp without emission in the UV-B range is used instead of the lamp which does emit UV-B radiation. For this purpose, a high brightness generated by the light by means of the lamp is advantageous, which can be generated for example by means of a full spectrum lamp or a white LED. Suitable irradiation intensities are for example at least 50 lux, more preferably at least 80 lux, especially preferably at least 100 lux. The daily irradiation in the day phase may to this end be carried out for example for at least 4 hours, preferably at least 10 hours and especially preferably at least 16 hours. The milk yield per animal may be increased for example by at least 2%, preferably at least 4%.

The hormone melatonin is important for organisms, which is why a suitable source would be desirable for this. It is known that the hormone melatonin is present in the milk of lactating animals. However, the components are normally relative low, so that ordinary milk is not suitable as a melatonin source. It has been shown that in a preferred embodiment of the method according to the invention it is also possible to obtain milk with a markedly increased melatonin content.

In the above-described preferred embodiment of the method according to the invention, in which the photoperiod of the animals is divided into a day phase with a first light regimen and a night phase with a second light regimen, the luminaire being employed for illumination purposes at least for some time during the day phase and a light source being employed during the night phase which emits light in the wavelength range of 500 nm or more and essentially no light in the wavelength range of below 500 nm, the milk in the night phase does not only have a high native vitamin D3 content, but also a high melatonin content. Milking the animals in the night phase or shortly after the night phase (for example up to 1 hour after the night phase) therefore results in a milk with a high native vitamin D3 content and an increased melatonin content. The melatonin in the milk is degraded relatively rapidly in the day phase as the result of the day-time illumination, so that milking for this purpose is carried out preferably shortly after the night phase, more preferably in the night phase. Naturally, this does not rule out milking in the day phase too; however, the milk obtained therefrom does not contain any elevated melatonin concentrations.

The invention also relates to the use of a luminaire comprising a lamp which emits UV-A radiation and UV-B radiation for irradiating one or more lactating animals in a roofed enclosure. All the information given hereinabove in respect of the method according to the invention naturally also apply correspondingly to the use according to the invention.

The invention also relates to a roofed enclosure for keeping lactating animals, at least one luminaire being fixed in the roofed enclosure which comprises a lamp which emits UV-A radiation and UV-B radiation, the luminaire preferably comprising a lamp cover which is permeable to UV-B radiation at a wavelength of 300 nm.

EXAMPLES

Comparative Examples 1 to 4

The milk produced in two pilot farms (farm I with 1100 dairy cows, farm II with 420 dairy cows) was examined in respect of its vitamin D concentration. The animals were kept in houses with stress-reducing free-range systems in which they were free to choose their own eating, drinking and lying-down places. Moreover, the animals were given grass- and herb-based feed rations. The animals were milked during the day and in some cases during the night phase. The animals were kept under the following photoperiod:

The duration of the day phase was approximately 16 hours. The duration of the night phase was approximately 8 hours. In the day phase, the animals were provided with visible light using commercially available fluorescent tubes arranged approx. 3 m above the floor of the animal house. The fluorescent tubes did not emit any radiation in the UV-B range. In the night phase, both groups of animals were kept under a light regimen with light with a wavelength of not below 500 nm. To this end, red LED lamps were employed.

After a habituation phase, milk collected at different days in farm I was examined for its vitamin D content (vitamin D3) by means of HPLC/UV (comparative examples 1 to 4). The results are shown in Table 1. The values agree with the values for the vitamin D content in commercially available milk (approx. 0.1 μg/100 ml milk according to Bundeslebensmittelschlüssel).

Examples 1 to 7

Operations in the two pilot farms continued in the same manner, except that the commercially available fluorescent tubes for the illumination in the day phase were replaced by luminaires with specific fluorescent lamps with a similar illumination intensity in the visible range. During the day, the animals were thus exposed to artificial light with a sunlight-like light spectrum. To provide the light, the full-spectrum lamps used were specific fluorescent lamps with the following emission spectrum:

| | |
|---|---|
| VIS component (380-780 nm) | approx. 90.85% |
| UV-A component (315-380 nm) | approx. 9% |
| UV-B component (280-315 nm) | approx. 0.15% |
| UV-C component (200-280 nm) | 0%. |

Figure 1:
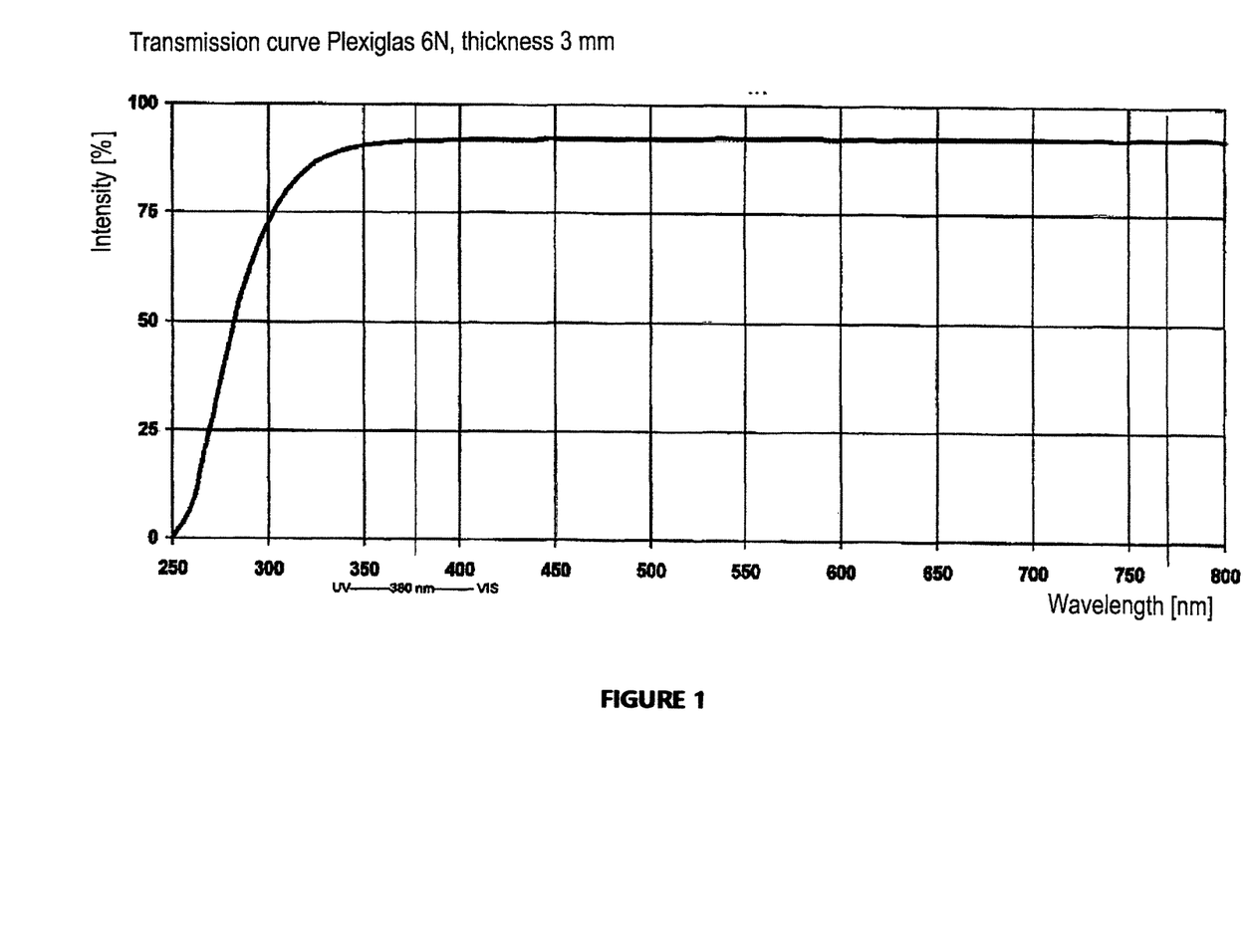
FIG. 1 shows a transmission curve of a specific plexiglass which is suitable as a lamp cover.
Figure 2:
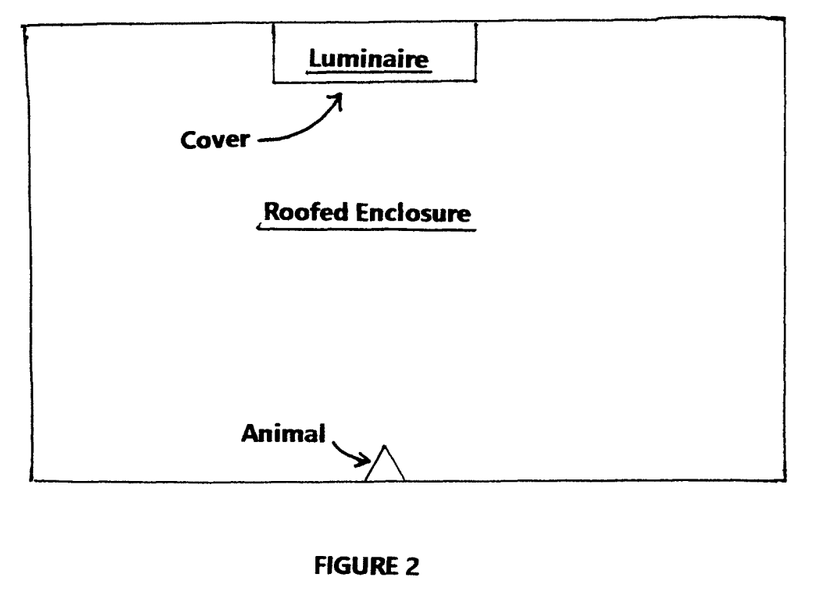
FIG. 2 is a schematic illustration of a facility for milk production in accord with the subject invention.

The illumination was effected daily using 2×58 watt full-spectrum fluorescent lamps arranged approx. 3 m above the floor of the animal house. The fluorescent lamps were IP 65-rated. The fluorescent lamps comprised a lamp cover. The lamp cover was formed from PMMA (Plexiglas 6N from Degussa) with a wall thickness of 3 mm. The FIGURE shows a transmission curve of the plexiglass of this wall thickness. At a wavelength of 300 nm, the degree of transmission was approx. 70%.

After a habituation phase under this photoperiod, the milk was examined on different days for its vitamin D content (vitamin D3) by means of ELISA (1 to 7). The milk produced in this manner contained a multiple of vitamin D in comparison with milk from traditional milk production. The vitamin D contents were 1.63 to 1.92 μg/100 ml milk. Table 1 shows the results of the samples in question, which had been taken from the respective milk tanks, and of mixed samples. The tanks and the mixed samples comprise the collected milk of several cows. The average fat content of the milk samples was approx. 4%.

TABLE 1

Vitamin D contents in the milk

| Sample No. | | Vitamin D3 content μg/100 ml milk |
|---|---|---|
| Comparative ex. 1 | Farm I, mixed sample | <0.2* |
| Comparative ex. 2 | Farm I, mixed sample | <0.2* |
| Comparative ex. 3 | Farm I, mixed sample | <0.2* |
| Comparative ex. 4 | Farm I, mixed sample | <0.2* |
| Example 1 | Farm II, mixed sample | 1.63 |
| Example 2 | Farm II, mixed sample | 1.87 |
| Example 3 | Farm I, tank 1 | 1.91 |
| Example 4 | Farm I, tank 2 | 1.92 |
| Example 5 | Farm I, tank 3 | 1.90 |
| Example 6 | Farm I, mixed sample | 1.75 |
| Example 7 | Farm I, mixed sample | 1.83 |

*below the detection limit

After a one-year operation according to the method according to the invention, the following other phenomena were able to be observed in comparison with the period before the method was introduced:

the incidence of disease and reproduction rates of the animals dropped, the farm's veterinary expenditure dropped, the milk production per animal increased by over 5%.

Examples 8 to 12

The operation in the two pilot farms was continued as described in Examples 1-7, except that the fluorescent lamps employed in Examples 1-7 for the illumination in the day phase were replaced by luminaires with specific fluorescent lamps with similar illumination intensity in the visible range. During the day, the animals were thus exposed to artificial light with a sunlight-like light spectrum. For generating the light, the full-spectrum lamps used were specific fluorescent lamps with an even higher UV-B component, which contained a mixture of approx. 36% SBPE, approx. 50% SMS, approx. 13% BAC and approx. 1% LAP as fluorescent substances. The fluorescent lamps had the following emission spectrum.

| | |
|---|---|
| VIS component (380-780 nm) | approx. 90% |
| UV-A component (315-380 nm) | approx. 9% |
| UV-B component (280-315 nm) | approx. 1% |
| UV-C component (200-280 nm) | 0%. |

The illumination was effected daily using 2×58 watt full-spectrum fluorescent lamps arranged approx. 3 m above the floor of the animal house. The fluorescent lamps were IP 65-rated. The fluorescent lamps comprised a lamp cover. The lamp cover was formed from PMMA (Plexiglas 6N from Degussa) with a wall thickness of 3 mm. The FIGURE shows a transmission curve of the plexiglass of this wall thickness. At a wavelength of 300 nm, the degree of transmission was approx. 70%.

After a habituation phase under this photoperiod, the milk was examined on different days for its vitamin D content (vitamin D3) by means of ELISA (Examples 8 to 12). The milk produced in this manner contained a multiple of vitamin D in comparison with milk from traditional milk production. The vitamin D contents were 2.34 to 2.67 μg/100 ml milk. Table 2 shows the results of the samples in question, which had been taken from the respective milk tanks. The tanks comprise the collected milk of several cows. The average fat content of the milk samples was approx. 4%.

TABLE 2

Vitamin D contents in the milk

| Sample No. | | Vitamin D3 content μg/100 ml milk |
|---|---|---|
| Example 8 | Farm I, tank 1 | 2.67 |
| Example 9 | Farm I, tank 2 | 2.67 |
| Example 10 | Farm I, tank 3 | 2.65 |
| Example 11 | Farm I, tank 4 | 2.55 |
| Example 12 | Farm I, tank 5 | 2.34 |

After a one-year operation according to the method according to the invention, the following other phenomena were able to be observed in comparison with the methods used for comparative Examples 1 to 4:

the incidence of disease and reproduction rates of the animals dropped, the farm's veterinary expenditure dropped, the milk production per animal increased by over 5%.

The invention claimed is:

1. A method for the production of milk with a high native vitamin D3 content, said method comprising providing a roofed enclosure including at least one luminaire comprising one lamp that is a full spectrum fluorescent lamp which emits VIS radiation, UV-A radiation and UV-B radiation, exposing at least one lactating animal to the full spectrum including the VIS, UV-A and UV-B radiation for between 6 and 22 hours daily such that a milk yield per lactating animal is increased and milking the animal, wherein a UV-B radiation component in an emission spectrum of the lamp is between at least 0.2% of an irradiation intensity of the lamp and less than 5% of the irradiation intensity of the lamp and wherein a radiation component in a VIS range in the emission spectrum of the lamp is at least 70%, wherein the at least one luminaire includes a lamp cover comprised of quartz glass, borosilicate glass, polymethyl methacrylate, polymethylpentene, fluorinated ethylene propylene, or polytetrafluoroethylene, said lamp cover being permeable to UV-B radiation having a wavelength of 300 nm, wherein the lamp cover is fixed to a housing of the luminaire, and a seal with talcum is arranged between the lamp cover and the housing.

2. The method according to claim 1, wherein the native vitamin D3 content of the milk is increased.

3. The method according to claim 1, wherein the UV-B radiation component in the emission spectrum of the lamp is at least 0.5% of the irradiation intensity of the lamp.

4. The method according to claim 1, wherein the fluorescent lamp is a low-pressure discharge lamp.

5. The method according to claim 1, wherein the lamp is a fluorescent lamp including at least one luminescent substance selected from strontium borophosphate:Eu, strontium magnesium phosphate:Sn, barium magnesium aluminate:Ce, and lanthanum phosphate:Ce.

6. The method according to claim 1, wherein a daily rhythm of the animal is divided into a day phase with a first light regimen and a night phase with a second light regimen, the luminaire being employed for illumination purposes at least for some time during the day phase.

7. The method according to claim 1, wherein the animal is a sheep, a goat or a cow.

8. The method according to claim 1, wherein the luminaire is dust-proof and protected against strong water jets.

9. A milk with a high native vitamin D3 content, obtained by the method of claim 1, wherein the vitamin D3 content is more than 1.5 μg/100 ml of milk.

10. The method according to claim 1, wherein the lamp has a color rendering index of greater than 40.

11. The method according to claim 1, wherein a daily rhythm of the animal is divided into a day phase with a first light regimen and a night phase with a second light regimen, and wherein a light source which emits light in a wavelength range of 500 nm or more with essentially no light in the wavelength range below 500 nm is employed during the night phase.

12. The method according to claim 11, wherein the light source used for the night phase is an LED lamp or a sodium vapor lamp.

13. The method of claim 1 wherein the VIS radiation is from 380 to 700 nm, the UV-A radiation is from 315 to 380 nm and the UV-B radiation is from 280 to 315 nm, and wherein the UV-A radiation is between at least 0.5% and less than 20% of the irradiation intensity of the lamp.

14. The method of claim 1 wherein the lamp includes fluorescent substances which generate, via physico-chemical processes, visible radiation in a wavelength range from 380 to 780 nm, UV radiation in a wavelength range of from 280 to 380 nm and in a wavelength range below 280 nm.

15. The method of claim 1 wherein the lamp is a three-band lamp which generates white light by mixing red, green and blue-emitting radiation, wherein a green-emitting fluorescent substance also emits in the UV-A range, and an Hg emission exists at 365 nm.

16. The method of claim 1 wherein the lamp includes fluorescent substances for UV-B selected from $SrAl_{12}O_{19}$:Ce, $LaB_3O_6$:Bi,Gd or $LaPO_4$:Ce.

17. The method of claim 1 wherein the luminaire does not include an LED lamp.

* * * * *